(12) United States Patent
Lee

(10) Patent No.: US 11,123,231 B2
(45) Date of Patent: Sep. 21, 2021

(54) DIAPER WITH WET DIAPER MONITORING DEVICE

(71) Applicant: Peter Lee, Huntington Beach, CA (US)

(72) Inventor: Peter Lee, Huntington Beach, CA (US)

( * ) Notice: Subject to any disclaimer, the term of this patent is extended or adjusted under 35 U.S.C. 154(b) by 173 days.

(21) Appl. No.: 16/336,055

(22) PCT Filed: Sep. 21, 2018

(86) PCT No.: PCT/US2018/052311
§ 371 (c)(1),
(2) Date: Mar. 22, 2019

(87) PCT Pub. No.: WO2020/060570
PCT Pub. Date: Mar. 26, 2020

(65) Prior Publication Data
US 2020/0360193 A1    Nov. 19, 2020

(51) Int. Cl.
*A61F 13/42* (2006.01)
*A61F 13/49* (2006.01)
*G08B 21/18* (2006.01)
*G08B 21/20* (2006.01)
*G01N 27/22* (2006.01)

(52) U.S. Cl.
CPC .............. *A61F 13/42* (2013.01); *A61F 13/49* (2013.01); *G01N 27/227* (2013.01); *G01N 27/228* (2013.01); *G08B 21/18* (2013.01); *G08B 21/20* (2013.01); *A61F 2013/424* (2013.01)

(58) Field of Classification Search
CPC .... A61F 13/42; A61F 13/49; A61F 2013/424; G01N 27/227; G01N 27/228; G08B 21/18; G08B 21/20
See application file for complete search history.

(56) References Cited

U.S. PATENT DOCUMENTS

| | | | | |
|---|---|---|---|---|
| 5,838,240 | A * | 11/1998 | Johnson | A61F 5/48 340/604 |
| 5,903,222 | A | 5/1999 | Kawarizadeh et al. | |
| 8,866,624 | B2 * | 10/2014 | Ales, III | A61B 5/6808 340/604 |
| 9,138,354 | B2 * | 9/2015 | Nhan | A61F 13/00055 |

(Continued)

FOREIGN PATENT DOCUMENTS

| KR | 20100103046 A | 9/2010 |
|---|---|---|
| WO | 2012/114208 A1 | 8/2012 |

(Continued)

*Primary Examiner* — Tung X Nguyen
*Assistant Examiner* — Feba Pothen
(74) *Attorney, Agent, or Firm* — Tsz Lung Yeung

(57) ABSTRACT

A diaper includes a diaper body and a wet diaper monitoring device, which includes a disposable pouch and a monitoring device. The monitoring device includes a monitoring casing, a first sensor electrode, a second sensor electrode, a sensing circuitry and an indicator. The first sensor electrode and the second sensor electrode are provided on an inner surface of and received in the monitoring casing, and form a single planar capacitor when the diaper body is dry. When the diaper body becomes wet, a capacitance between the first sensor electrode and the second sensor electrode increases substantially so as to transform the single planar capacitor of the first sensor electrode and the second sensor electrode into two much larger series connected capacitors.

4 Claims, 18 Drawing Sheets

(56) References Cited

U.S. PATENT DOCUMENTS

| | | | |
|---|---|---|---|
| 9,907,707 B2* | 3/2018 | LaVon | ................. A61F 13/505 |
| 2010/0042346 A1* | 2/2010 | Kuang | ................. H03K 17/962 |
| | | | 702/65 |
| 2011/0012618 A1 | 1/2011 | Teterwak et al. | |
| 2011/0102217 A1 | 5/2011 | Hsu | |
| 2015/0160148 A1* | 6/2015 | Stanley | ................. G01N 27/228 |
| | | | 324/686 |

FOREIGN PATENT DOCUMENTS

| | | |
|---|---|---|
| WO | 2017/003390 A1 | 1/2017 |
| WO | 2017/152687 A1 | 9/2017 |

* cited by examiner

DIAPER WITH WET DIAPER MONITORING DEVICE

BACKGROUND OF THE PRESENT INVENTION

Field of Invention

The present invention relates to a diaper, and more particularly to a diaper comprising a wet diaper monitoring arrangement which is capable of detecting and alerting users when the diaper becomes wet.

Description of Related Arts

Two common wet diaper detection methods are used in prior arts. They are conductance sensor detection method and capacitance sensor detection method.

Conductance sensor detection method generally relies on the detection of small amount of current flows across a sensing element when wetness is detected. Typically, this type of sensing element consists of two parallel conductors or wires imbedded between an inside layer and an outside layer of a diaper. Urine is a good conductive fluid. When the diaper is soiled, urine causes current to flow between the two conductors or wires. Conductance sensor imbedded in the diaper layers requires special manufacturing process that leads to high production cost.

On the other hand, various capacitance sensor designs were discussed in prior arts. For example, the general capacitance sensor design principle was described in U.S. Pat. No. 8,866,624 issued to Ales, III et al., U.S. Pat. No. 5,903,222 issued to Kawarizadeh, and U.S. Pat. No. 5,469,145 issued to Johnson. These referenced inventions used two or more metallic electrodes etched on a standard or flexible printed circuit board (PCB) forming a capacitor whose capacitance value depends on the dielectric constant (E) of the material between the two electrodes. The capacitance sensor is fastened on the outer surface of a diaper, so it could sense the change in dielectric constant of the diaper's inner layer when soiled. Dielectric constant of the diaper's inner layer increases by a factor of 10 or more when soiled.

Four type of capacitor sensor detection methods are generally used in prior arts to detect capacitance change due to a wet diaper condition:

1. Detection of frequency shift in a LC resonant circuit or a RC oscillator circuit where sensor capacitance is part of the circuit;
2. Detection of impedance changes in a LC tank circuit where sensor capacitance is part of the circuit;
3. Analog voltage amplitude detection of a sensor capacitance coupled signal; and
4. Measure the rise time of the capacitance sensor using a precision current source.

The first three detection methods are inherently analog in nature and which are less precise and less repeatable than digital method. Furthermore, analog detection circuits are also need more power despite some mitigating designs such as a low duty cycle detection method where the measurement circuit is only active for a very short period of time. Large power consumption is not desirable for a battery powered device. Rise time measurement method can either be analog or digital method. A separate analog to digital converter device is needed for digital measurement method.

In prior arts, many monitoring device electronics and the sensing element are two separate parts. They need to be linked together, both mechanically and electrically, via simple mechanical connectors such as metallic snap, clip or fastener. The monitoring device is typically clipped onto the diaper surface or the diaper edge. Therefore, the parent or caretaker must engage or disengage these mechanical connectors on every use. The process can be tedious, but it allows the monitoring device to be reused while discarding the disposable sensing element.

Due to the use of the snap and clip, most monitoring devices of this kind are not protected against contamination by urine or feces in an accidental spill. A thorough cleaning is required after such an incident—a process not very appealing to the parent or a care taker.

Other sensing elements proposed in prior arts include: chemical sensor, temperature sensor, optical sensor, etc. Most of these sensing elements are not very popular primarily due to their high cost.

The following patents are pertaining to the present invention:

U.S. Pat. No. 5,469,145 to Johnson describes a wet diaper detector using either resistive sensor or capacitive sensor. When a capacitive sensor is used, the sensor couples a pulse signal to a voltage sensitive threshold detection circuit. The coupled pulse signal is proportional to the sensor capacitance. The threshold detection circuit consists of an op-amp and a voltage comparator. Op-amp amplifies the coupled pulses to a more suitable voltage level so it can be peak detected. The detected peak signal is fed to a voltage comparator for making voltage threshold detection. This detection method is a pure analog in nature.

U.S. Pat. No. 5,903,222 to Kawarizadeh et al. describes an enclosed wet garment detector using a capacitive sensor. This sensor and its associated electronics are placed inside a housing. However, it is noted there is an air gap between the sensor electrodes the housing interior surface. Any such air gap would reduce sensor sensitivity as its dielectric constant is very close to "1".

It uses the same voltage threshold detection principle as the 145 patent where the coupled pulse signal by the sensor is amplified and peak detected for voltage threshold detection. The circuit requires manual adjustments during production for proper circuit performance.

U.S. Pat. No. 8,866,624 to Ales, III et al. describes various open face sensor electrode designs and general methods to detect capacitance change.

U.S. Pat. No. 9,241,839 to Abraham et al. describes a linear sensor array to detect wetness level. Sensor array consists of several identical sensor electrodes arranged in a linear manner such that different part of a diaper can be monitored.

U.S. Patent application 2007/0024457 to Long et al. describes various mechanical methods of removably affixing a device to the sensor element.

U.S. Pat. Nos. 8,416,088 and 8,111,165 to Ortega et al. describes a patient monitoring system for sensing pressure and wetness on a human body. It describes a device fabricated on a flexible circuit board substrate, so the finished device can be adhered or placed on a human body. The device contains a signal processing circuit and a RF transmitter circuit for sending a wireless signal to a remote receiver. A resistance sensor was described for urine detection.

U.S. Pat. No. 9,107,776 to Bergman et al. describes an elaborate incontinence management system and a custom designed diaper where numerous sensors were imbedded inside. The system provides a software estimate of a wetness event based on various sensor inputs. A resistance sensor was described, and it needs to encounter liquid such as urine to sense a wet condition.

U.S. Pat. No. 8,471,715 to Solazzo et al. describes a custom designed disposable diaper with an imbedded resistance wire sensor and a removable, reusable battery powered sensor-transmitter device. The reusable sensor-transmitter portion must be manually connected to the imbedded resistance wire sensor after each diaper change.

U.S. Pat. No. 6,603,403 to Jeutter et al. describes a wetness monitoring method of an absorbent article consisting of an imbedded passive transponder/sensor device which receives electrical energy from an external interrogator device. Both interrogator circuit and transponder/sensor circuit must be near each other so that electrical energy at a specific frequency can be transferred via an antenna coupling circuit within each device. This is essentially a RFID device (Radio Frequency Identification) with an external interrogation detector.

U.S. Pat. No. 6,774,800 to Friedman et al. describes a patient incontinence monitoring apparatus using RFID tag technology where a passive RFID tag is placed on a disposable diaper. An external interrogation device is needed to provide an excitation signal to power the RFID tag. The same interrogation device must read and decode the return signal on the wetness condition of the diaper.

U.S. Pat. No. 8,314,284 to Novella describes a diaper change alerting device for a custom implemented disposable diaper with a built-in pouch. The pouch houses the electronic device and is made of liquid permeable material, so urine can enter. When urine permeates into the pouch, the electronic device sensor detects a change in resistance or conductivity and acts accordingly to activate a built-in music speaker. The electronic sensor must be removed and cleaned before introduction into a new diaper.

U.S. Pat. No. 9,278,033 to Abraham et al. also describes an imbedded LC resonant circuit for RFID application. It requires an external interrogation device to detect the change in diaper wetness.

U.S. Pat. No. 7,145,053 to Emenike et al. describes diaper moisture indicator device with audible and display output. The invention is designed to clip onto a diaper outer surface. The invention relies on the detection of resistance drop across two sensing terminals caused by urine intrusion into a measurement sensor gap. Both unit and its sensor need to be cleaned after each use.

U.S. Pat. No. 6,870,479 to Gabriel describes a custom implemented disposable diaper with built in wire mesh as a resistance sensor. A wet diaper condition causes resistance to drop and a processor can detect such a change in resistance or conductivity.

U.S. Pat. No. 7,221,279 to Nielsen describes a monitoring system consisting of two portions: a disposable sensor unit and a reusable monitor/indicator unit. Both units are electrical connected via a connector. The sensor unit is essentially a resistance sensor placed inside a diaper, so it absorbs a small portion of any urine volume.

U.S. Patent application 2008/0278337 to Huang describes a urine detection system utilizing two flexible printed circuit substrates with etched capacitance sensor electrodes. One circuit substrate is placed inside the diaper and the other is placed on the outside of the diaper, but the two substrates need to precisely align for maximum capacitance effect.

U.S. Patent application 2009/0124990 to Feldkamp et al. describes an induction coil wetness sensor. The sensor consists of an LC resonant tank circuit. The tank circuit impedance changes as wetness level increases inside the diaper. The change is reflected on the DC output level of a marginal oscillator circuit.

U.S. Pat. No. 9,820,891 to Eyall describes a capacitance and photo detector method to detect a soiled diaper condition.

Other reference patents which may be pertinent to the present invention:

| | |
|---|---|
| U.S. Pat. No. 9,278,033 | Abraham |
| U.S. Pat. No. 9,241,839 | Abraham |
| U.S. Pat. No. 9,107,776 | Bergman |
| U.S. Pat. No. 8,866,624 | Ales, III |
| U.S. Pat. No. 8,111,165 | Ortega |
| U.S. Pat. No. 8,416,088 | Ortega |
| U.S. Pat. No. 8,471,715 | Solazzo |
| U.S. Pat. No. 8,314,284 | Novella |
| U.S. Pat. No. 7,221,279 | Nielsen |
| U.S. Pat. No. 7,145,053 | Emenike |
| U.S. Pat. No. 6,870,479 | Gabriel |
| U.S. Pat. No. 6,603,403 | Jeutter |
| U.S. Pat. No. 6,774,800 | Friedman |
| U.S. Pat. No. 5,903,222 | Kawarizadeh |
| U.S. Pat. No. 5,469,145 | Johnson |
| U.S. Pat. No. 5,264,830 | Kline |
| U.S. Pat. No. 7,221,279 | Nielsen |
| U.S. Pat. No. 8,299,317 | Tippey |
| U.S. Pat. No. 9,820,891 | Eyall (Light and capacitance) |
| U.S. Pat. No. 9,709,614 | Bruwer (Asoteq) |
| U.S. Pat. No. 9,831,864 | Thiagarajan (switched cap) |
| U.S. Pat. No. 9,817,537 | Shakya |
| U.S. Pat. No. 9,811,219 | Noto |
| U.S. Pat. No. 7,148,704 | Philipp |
| U.S. Pat. No. 6,466,036 | Philipp (Atmel) |
| U.S. Pat. No. 4,806,846 | Kerber |
| U.S. 2005/0046578A1 | Pires |
| U.S. 2007/0024457A1 | Long |
| U.S. 2008/0278337A1 | Huang |
| U.S. 2009/0124990A1 | Feldkamp |
| U.S. 2010/0168694 A1 | Gakhar |
| U.S. 2015/0080819A1 | Charna |
| U.S. 2017/0250661A1 | Imaizumi |
| U.S. 2017/0264309 A1 | Wada |
| U.S. 2017/0308106 A1 | Ates |
| U.S. 2017/0323134A1 | Yeo |
| U.S. 2017/0331366A1 | Awad |

Baby Diaper Wetness Detector and Indicator—A Senior Design Project from The City College of New York, by Ndaw et al. February 2008.

MTCH112 Dual-Channel Proximity/Touch Controller datasheet by Microchip Technology Inc., DS41668A-page 28, 2012.

SUMMARY OF THE PRESENT INVENTION

Certain variations of the present invention provide a diaper comprising a wet diaper monitoring arrangement which is capable of detecting and alerting users when the diaper becomes wet.

Certain variations of the present invention provide a diaper comprising a first sensor electrode and a second sensor electrode so that when a diaper becomes wet, the capacitance between the first sensor electrode and the second sensor electrode increases substantially so as to transform the single planar capacitor of the first sensor electrode and the second sensor electrode into two much larger series connected capacitors.

Certain variations of the present invention provide a diaper comprising a wet diaper monitoring arrangement which utilizes different alternatives of switch capacitor circuit to detect and determine whether or not a diaper body has become wet.

In one aspect of the present invention, it provides a diaper, comprising:

a diaper body; and a wet diaper monitoring arrangement, which comprises:

a disposable pouch detachably attached on a front portion of the diaper body, the disposable pouch having a receiving cavity; and a monitoring device, which comprises:

a monitoring casing provided in the receiving cavity at a position adjacent to an inner surface of the disposable pouch;

a first sensor electrode and a second sensor electrode spacedly provided on an inner surface of and received in the monitoring casing, the first sensor electrode and the second sensor electrode forming a single planar capacitor when the diaper body is dry;

a sensing circuitry received in the monitoring casing and electrically connected to the first sensor electrode and the second sensor electrode; and an indicator supported by the monitoring casing and electrically connected to the sensor circuitry, wherein when the diaper body becomes wet, a capacitance between the first sensor electrode and the second sensor electrode increases substantially so as to transform the single planar capacitor of the first sensor electrode and the second sensor electrode into two much larger series connected capacitors, the substantial change in the capacitance being arranged to be detected by the sensing circuitry which drives the indicator to indicate a corresponding wet signal of the diaper.

In another aspect of the present invention, it provides a wet diaper monitoring arrangement for a diaper comprising a diaper body having an inner layer, an outer layer, and an absorbent layer sandwiched between the inner layer and the outer layer, the wet diaper monitoring arrangement comprising:

a disposable pouch configured for affixing on a front portion of the diaper body, the disposable pouch having a receiving cavity; and a monitoring device, which comprises:

a monitoring casing provided in the receiving cavity at a position adjacent to an inner surface of the disposable pouch;

a first sensor electrode and a second sensor electrode spacedly provided on an inner surface of and received in the monitoring casing, the first sensor electrode and the second sensor electrode forming a single planar capacitor when the diaper body is dry;

a sensing circuitry received in the monitoring casing and electrically connected to the first sensor electrode and the second sensor electrode; and an indicator supported by the monitoring casing and electrically connected to the sensor circuitry, wherein when the diaper body becomes wet, the absorbent layer being converted from an insulating layer to a conductive layer so that a capacitance between the first sensor electrode and the second sensor electrode increases substantially so as to transform the single planar capacitor of the first sensor electrode and the second sensor electrode into two much larger series connected capacitors, the substantial change in the capacitance being arranged to be detected by the sensing circuitry which drives the indicator to indicate a corresponding wet signal of the diaper.

This summary presented above is provided merely to introduce certain concepts and not to identify any key or essential features of the claimed subject matter.

DETAILED DESCRIPTION OF THE PREFERRED EMBODIMENT

Figure 1:
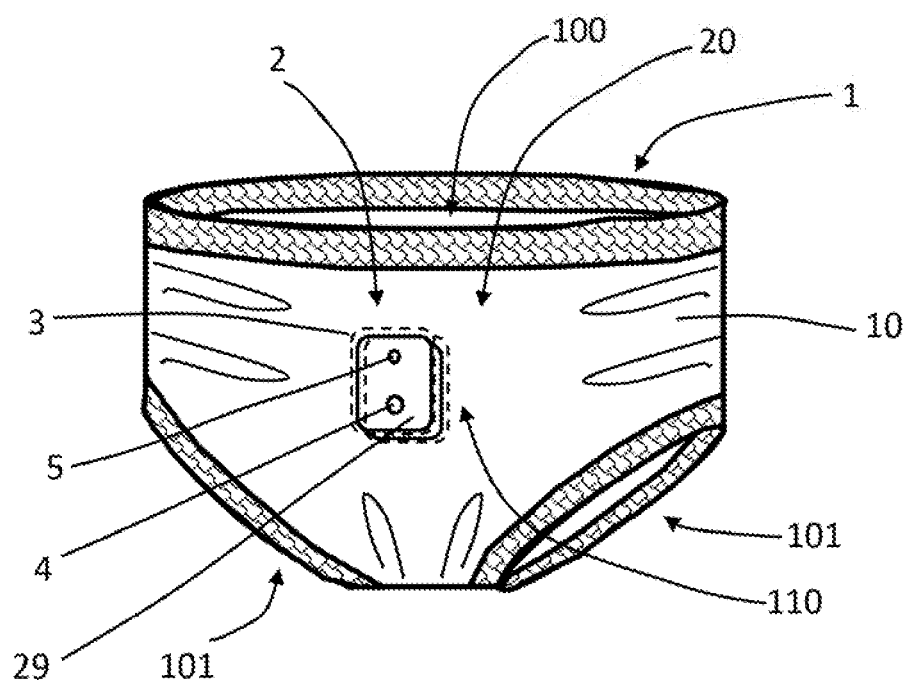
FIG. 1 is a front schematic view of a diaper with an attached wet diaper monitoring arrangement according to a preferred embodiment of the present invention.

The following detailed description of the preferred embodiment is the preferred mode of carrying out the invention. The description is not to be taken in any limiting sense. It is presented for the purpose of illustrating the general principles of the present invention.

Referring to FIGS. 1 to 21 of the drawings, a diaper according a preferred embodiment of the present invention is illustrated. Broadly, the diaper 1 may comprise diaper body 10 and a wet diaper monitoring arrangement 20 provided on the diaper body 10.

The wet diaper monitoring arrangement 20 may comprise a disposable pouch 3 and a monitoring device 2. The monitoring device 2 may comprise a monitoring casing 29, a first sensor electrode 7, a second sensor electrode 8, a sensing circuitry 12, and an indicator 5.

The disposable pouch 3 may be detachably affixed on a front portion 110 of the diaper body 10. The disposable pouch 3 may have a receiving cavity 33.

The monitoring casing 29 may be provided in the receiving cavity 33 at a position adjacent to an inner surface 31 of the disposable pouch 3.

The first sensor electrode 7 and the second sensor electrode 8 may be spacedly provided on an inner surface of and received in the monitoring casing 29. The first sensor electrode 7 and the second sensor electrode 8 may form a single planar capacitor when the diaper body 10 is dry.

The sensing circuitry 12 may be received in the monitoring casing 29 and electrically connected to the first sensor electrode 7 and the second sensor electrode 8. The sensing circuitry 12 may be implemented on a Printed Circuit Board (PCB 13).

The indicator 5 may be supported by the monitoring casing 29 and electrically connected to the sensor circuitry 12. When the diaper body 10 becomes wet, a capacitance between the first sensor electrode 7 and the second sensor electrode 8 increases substantially so as to transform the single planar capacitor of the first sensor electrode 7 and the second sensor electrode 8 into two much larger series connected capacitors, wherein the substantial change in the capacitance may be detected by the sensing circuitry 12 which drives the indicator 5 to indicate a corresponding wet signal of the diaper of the present invention.

In the preferred embodiment of the present invention, FIG. 1 illustrates the attachment of the wet diaper monitoring arrangement 20 on the diaper body 10. The first sensor electrode 7 and the second sensor electrode 8 may be adapted to detect a soiled condition when urine or other body fluid is present in the diaper body 10. The diaper body 10 may be configured as having a 3-layer absorbent structure and comprise an inner layer 9, an absorbent layer 10, and an outer layer 11. The inner layer 9 may channel urine or other body fluid away from skin while maintaining a dry feeling to the wearer. The absorbent layer 10 may be formed between the inner layer 9 and the outer layer 11 for absorbing urine or the body fluid exuded by the wearer. The outer layer 11 may be configured as a protective layer that keeps urine and body fluid from leaking out. The diaper body 10 may have a wearing cavity 100 for allowing a wearer to wear on, and a plurality of leg openings 101 for allowing the wearer's legs to pass therethrough. The diaper body 10 may be made of flexible and soft material for imparting maximal comfort to the wearer.

The disposable pouch 3 of the wet diaper monitoring arrangement 20 may be made of flexible plastic material and may be shaped and sized for enclosing the monitoring device 2. The disposal pouch 3 may have two important surfaces, an inner surface 31 and an outer surface 32. The inner surface 31 may be coated with an adhesive layer 6 with a peel-off cover (not shown), while the outer surface 32 may be linked to a flap 14. Upon inserting the monitoring device 2 into the pouch 3, the flap 14 may be folded over and sealed against the upper edge portion 61 of the adhesive layer 6 forming an enclosed pouch assembly. This enclosed pouch assembly may be affixed to an exterior surface on the front portion 110 of the diaper body 10 using the remainder of the adhesive layer 6.

Figure 5:
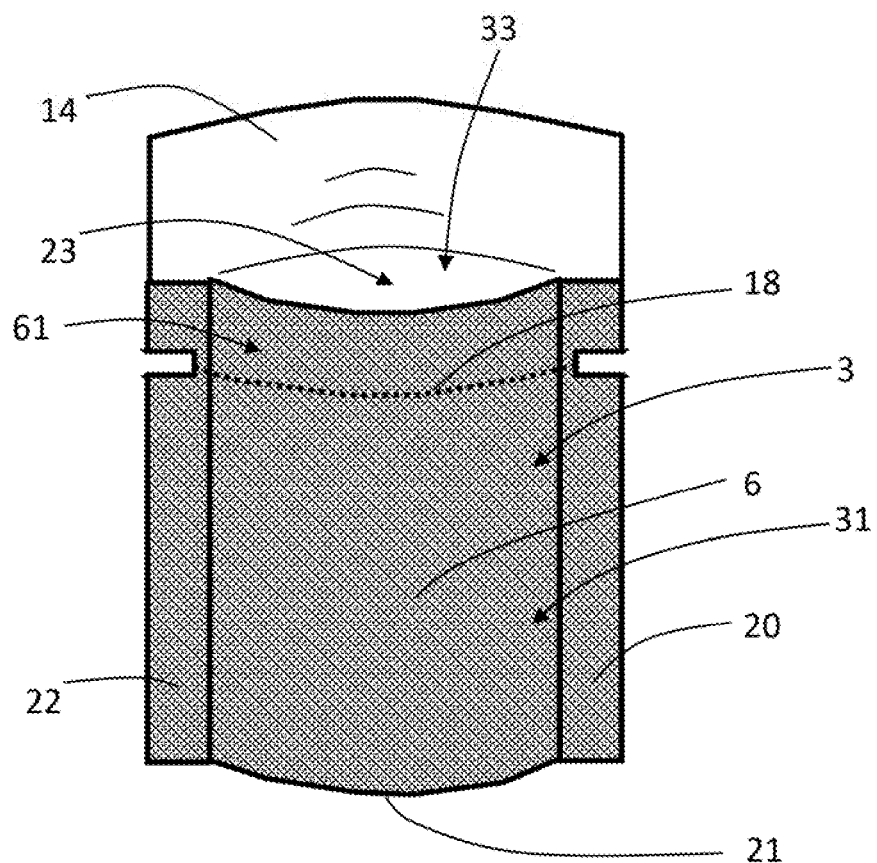
FIG. 5 is a rear view of a disposable pouch according to the preferred embodiment of the present invention.

FIG. 5 illustrates the construction details of disposable pouch 3. It is formed by folding a properly shaped and sized piece of plastic sheet together and then heat sealing the two sides 20, 22 together for forming a pouch structure. Plastic sheet is stretchable and is low cost. The disposable pouch 3 may have an opening 23 with a flap 14 and a closed-end 21. The inner surface 31 may be smaller in area and may be have the adhesive layer 6 coated thereon. The outer surface 32 may be connected to the flap 14. A perforated line 18 may be incorporated on the inner surface 31 and the outer surface 32 of the disposable pouch 3. This creates an easy tear-off feature facilitating the retrieval of the wet diaper monitoring device 2 during a diaper change.

During normal use, the monitoring device 2 may be inserted into the disposable pouch 3 via the opening 23 such that the inner surface of the monitoring casing 29 may be adjacent to the inner surface 31 of the disposable pouch 3. The flap 14 may then be folded over and sealed against the top edge portion 61 of the adhesive layer 6 so as to form the enclosed pouch assembly. The disposable pouch 3 may be affixed to the outer surface of the front portion 110 of the diaper body 10 using the remainder of adhesive layer 6.

In addition to offering protection against potential urine and feces contamination, the disposable pouch 3 may be sized so that its stretchable property may exert a constant compression force on monitoring device 2 (and the monitoring casing 29) at all time. This constant compression force serves an important function to minimize the formation of any air pocket between disposable pouch 3 and the monitoring casing 29. Since the first sensor electrode 7 and the second sensor electrode 8 may be mounted in direct contact with the inner surface interior of monitoring casing 29, any air pocket formation could alter sensor capacitance reading as air has a different dielectric constant (E=1) than that of the pouch plastic (E approximately equals to 2.2). Once an air pocket was inadvertently created, the size of this air pocket may change or move around due to the physical movements of the wearer. The formation or any change in air pocket can create an inaccurate reading on the sensor capacitance value. A constant compression force may eliminate this possibility.

The disposable pouch 3 may be affixed to an exterior surface on the front portion 110 of the diaper body 10 using the peel-off adhesive technique. The monitoring device 2 may further comprise a pushbutton 4 provided on the monitoring casing 29 and electrically connected to the sensing circuitry 12. The indicator 5 may be configured as a Light Emitting Diode (LED) and may provide a visual operating status of the monitoring device 2. For example, a slow blinking green color generated by the LED may indicate that monitoring device 2 is operating normally and the diaper body 10 is dry. A fast blinking red color generated by the LED may indicate that the diaper body 10 is wet and needs to be changed. Furthermore, an alternating red and green blinking generated by the LED may indicate that the battery level is low and the battery needs to be replaced.

The pushbutton 4 may be configured as a momentary switch for initializing a new monitoring process after completing a diaper change. Upon activation, software program (described below) of the monitoring device 2 may perform four consecutive capacitance sensor readings and saves the average of these four readings as the digital baseline reference value. All future sensor readings will be compared against this reference value. The mechanism of these calculation will be described in more details below.

Figure 2:
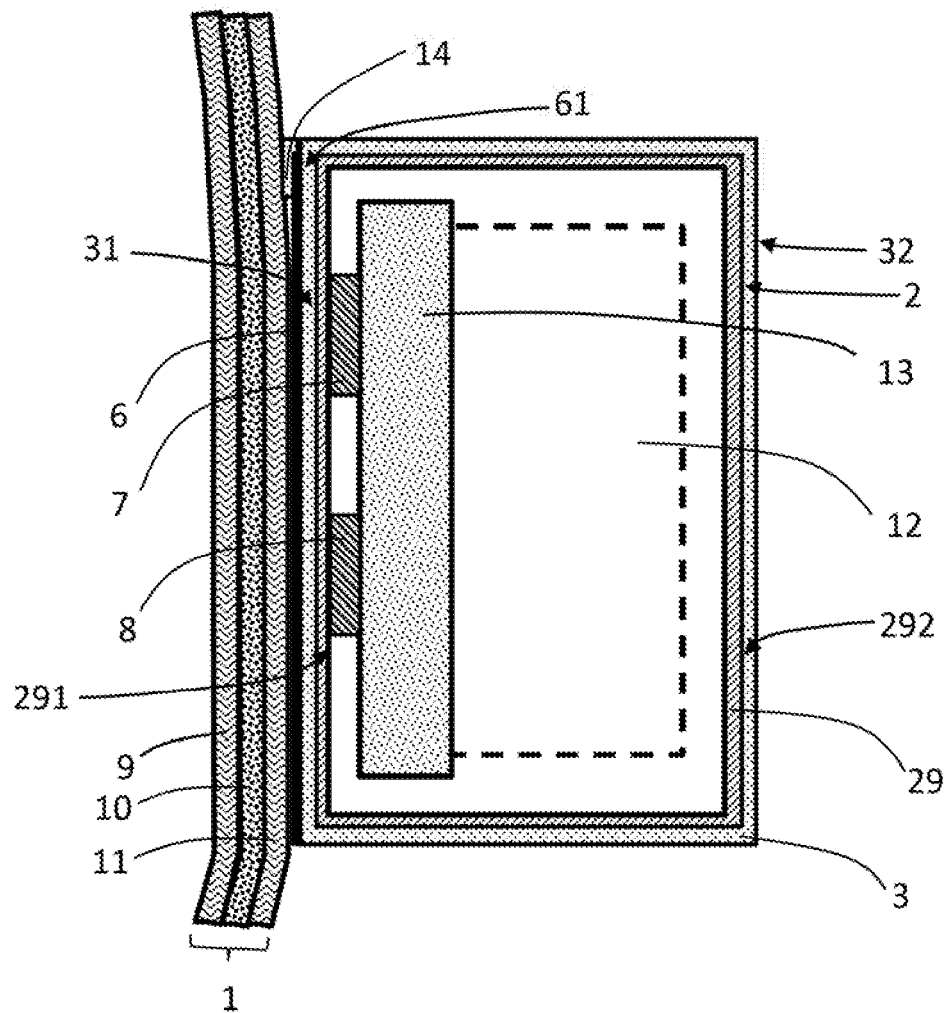
FIG. 2 is a cross-sectional side view of the diaper with the wet diaper monitoring arrangement according to the preferred embodiment of the present invention.

Referring to FIG. 2 of the drawings, it illustrates that the monitoring device 2 may be enclosed within the disposable pouch 3 and then sealed by using the flap 14. This forms an enclosed pouch assembly. The monitoring casing 29 may have a first casing surface 291 and a second casing surface 292. The first casing surface 291 may be defined as the inner surface that is placed closest to the diaper body 10 while the second casing surface 292 may be defined as the outer surface which is opposite to the first casing surface 291.

Figure 3:
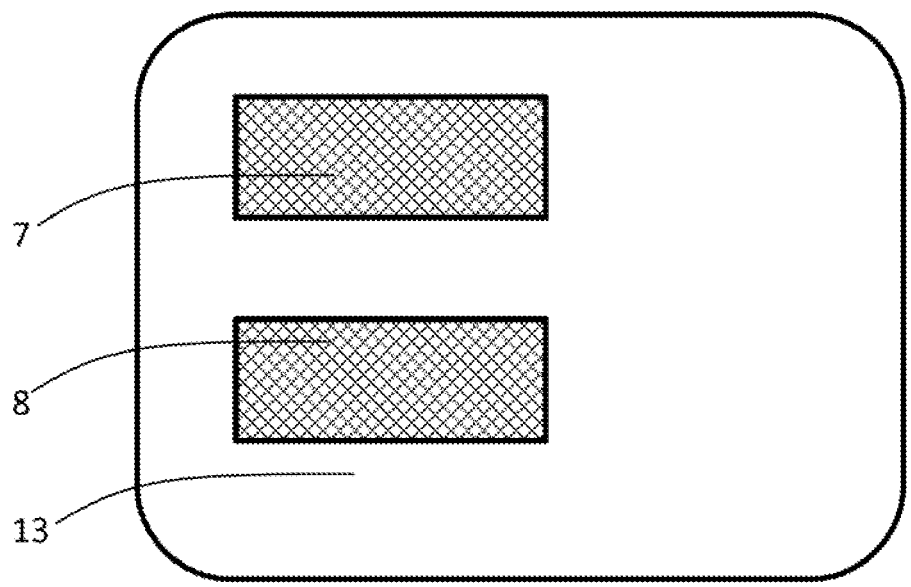
FIG. 3 is a schematic diagram of a monitoring device according to the preferred embodiment of the present invention, illustrating a PCB and two sensor electrodes.

The first sensor electrode 7 and the second sensor electrode 8 may be etched on one side of the PCB 13 and are placed in direct contact against the first casing surface 291 of the monitoring casing 29. The sensing circuitry 12 may comprise a plurality of electronic components which will be described below. The electronic components may be mounted on the PCB 13 and may be oriented away from the first sensor electrode 7 and the second sensor electrode 8. FIG. 3 illustrates a front view of the first sensor electrode 7 and the second sensor electrode 8, each measuring approximately 10 mm by 25 mm in surface area and spaced 5 mm from each other.

There are different methods to evaluate a new sensor reading by the software program. A simple method is to compare the new reading against the digital baseline reference value to determine wetness level. For example, the diaper body 10 is deemed to be soiled if a new reading exceeds the digital baseline reference value by 50% (or other percentage value as appropriate). The software flow chart of this method may be illustrated in FIG. 17. An alternate software flow chart may be illustrated in FIG. 18, where the average of the four latest sensor readings is calculated and saved as the new base-reference value. This approach can compensate for slow change due to temperature effect. Since a soiled diaper is likely to stay wet for a while, note that both software flow charts require the soiled condition to last at least 3-seconds or longer before activating alerting outputs.

Instead of comparing against a calculated digital baseline reference, an even simpler method is for each new reading to be compared against a fixed digital number imbedded in the software program. If a new reading exceeds this fixed digital number by a fixed value or more, then the diaper is soiled. When a soiled condition is detected, software program may activate the indicator 5 to show red color while simultaneously send out a wireless signal via a built-in wireless RF transmitter 25. Additional audio alerting device such as a speaker can also be activated for local alerting. Thus, the monitoring device 2 may further comprise a wireless Radio Frequency (RF) transmitter 25 electrically connected to the sensing circuitry 12 for transmitting RF signal.

Software program may determine how frequent a new reading is to be taken. To minimize battery drain, the software program can vary the period between readings according to a simple variable time format. For example, the software program may initiate a new reading every 10 minutes during the first 30 minutes after a diaper change, then change to performing a new reading every five (5) minutes during the next 30 minutes, and finally change to performing a new reading every minute until a soiled diaper condition is detected. The software program is flexible enough so the parent or a caretaker can override this variable time reading format to a constant one (1) minute reading format. A user of the present invention may accomplish this by pressing and holding the pushbutton 4 for a predetermined period of time (such as 10 seconds) until the software program acknowledges this change by providing a temporarily blinking green color through the indicator 5. Moreover, pressing and holding the pushbutton 4 for another predetermined period of time may toggle the setting back to the variable time reading format again. Thus, the user of the present invention may be set to be in full control of selecting the most effective reading interval for each individual circumstance.

As an exemplary embodiment, when the diaper is dry, the planar capacitance between the two sensor electrodes may be estimated using the following formula:

$$C = \epsilon_o \epsilon_r (t*l)/d, \text{ where}$$

$\epsilon_o$=permittivity in vacuum=8.85 pf/m $\epsilon_r$=relativity permittivity (dielectric constant)=4.4 (for FR4 PCB)

t=the thickness of the electrode=0.035 mm (base on a 1 oz copper PCB)

l=the length of the electrode=25 mm d=the separation distance between the electrodes=5 mm C=0.0068 pf, in which this is an extremely small value and circuit parasitic capacitance will dominate. Parasitic in the range of up to 2 pf is expected in real circuit operation.

Dry diaper sensor capacitance=C dry=parasitic capacitance=2 pf

Figure 4:
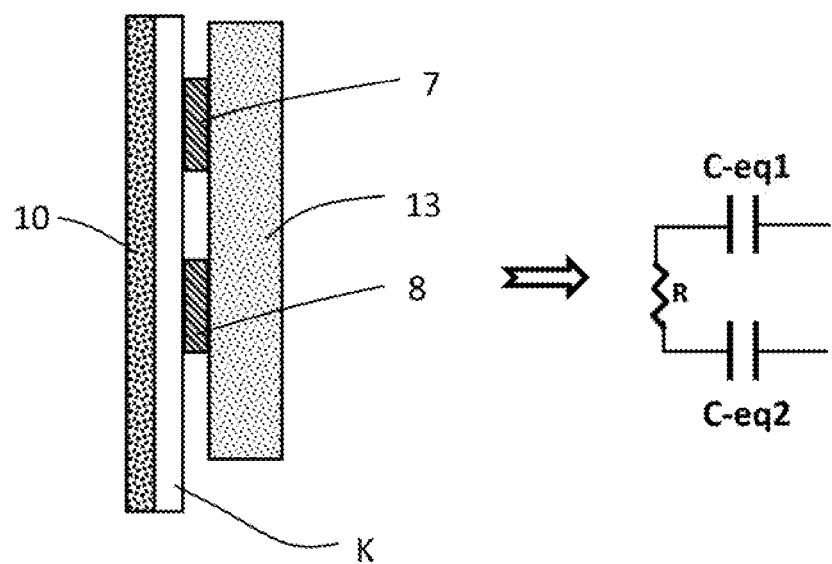
FIG. 4 is a schematic diagram of a wet diaper monitoring device according to the preferred embodiment of the present invention, illustrating a simplified view of FIG. 2 and two equivalent capacitors formed by two electrodes when the diaper is wet.

Urine is a good conductor. When the diaper body 10 becomes wet, the absorbent layer 10 may change from an insulator layer to a conductive layer. This effectively changes a single planar capacitor into two large series connected capacitors as shown in FIG. 4. A new capacitor is formed between each electrode and the wet absorbent layer 10, separated by insulator layer 11. The surface area of each of the two new capacitors is 250 sq. mm which is 285 times larger than that of the original planar capacitor. Therefore, a wet diaper transforms the first sensor electrode 7 and the second sensor electrode 8 from a single planar capacitor into two much larger series connected capacitors.

FIG. 4 illustrates a simplified view of FIG. 2 when the diaper body 10 is wet. As shown in FIG. 4 of the drawings, K represents the total thickness of the disposable pouch 3 and the monitoring casing 29, the adhesive layer 6, and the outer layer 11 of the diaper body 10. The first sensor electrode 7 and the second sensor electrode 8 may be arranged to make direct contact against the monitoring casing 29 so that there is no air gap between the first and the second sensor electrode 7, 8 and the monitoring casing 29. This arrangement may minimize k and maximize $\epsilon_r$ on the capacitance formula below, and may produce a larger sensor capacitance change when the diaper body 10 changes from dry to wet. The first sensor electrode 7 and the second sensor electrode 8 and the inner layer 10 of the diaper body 10 may form two equivalent capacitors, C-eq1 and C-eq2 as shown below.

The capacitance, C, of the two electrodes shown in FIG. 4 can be estimated using the following formula:

$$C = C\text{-}eq1 = C\text{-}eq2 = \epsilon_o \epsilon_r (x*l)/d$$

Where,

εo=permittivity in vacuum=8.85 pf/m

εr=relativity permittivity (dielectric constant) of layer k~=2.2 (for plastic)

x=the width of the electrode=10 mm l=the length of the electrode=25 mm d=K=the distance between each electrode to the wetted diaper layer ~=0.75 mm C=6.5 pf for each electrode; or C wet=3.25 pf total since they are in series.

Wet diaper sensor capacitance=C wet+C dry=3.25 pf+2 pf=5.25 pf

In this preferred embodiment, the present invention utilizes a Switch Capacitor Circuit (SCC) that consists of a single capacitor, two transistors, and two non-overlapping clock signals for converting a sensor capacitance into a digital equivalent value suitable for digital signal processing. A switched capacitor circuit (SCC) is an electronic circuit technique used for discrete-time signal processing. SCC works by moving charges of an electrical-signal into and out of capacitors when transistor switches are opened and closed by clock signals. Usually, non-overlapping clock signals are used to control the transistor switches, so that not all switches are closed simultaneously.

Figure 6:
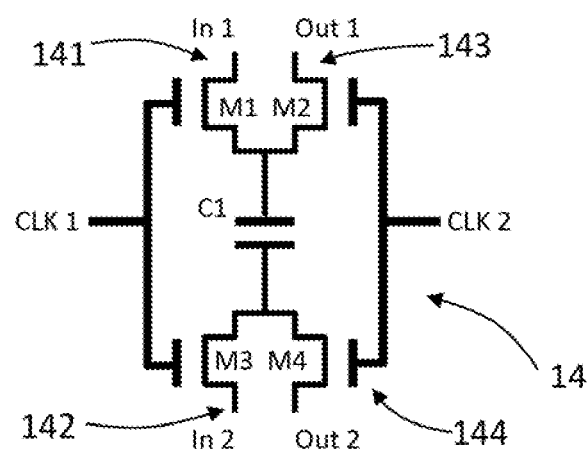
FIG. 6 is a schematic diagram of a four transistor Switched Capacitor Circuit (SCC) driven by two non-overlapping clocks according to the preferred embodiment of the present invention.
Figure 7:
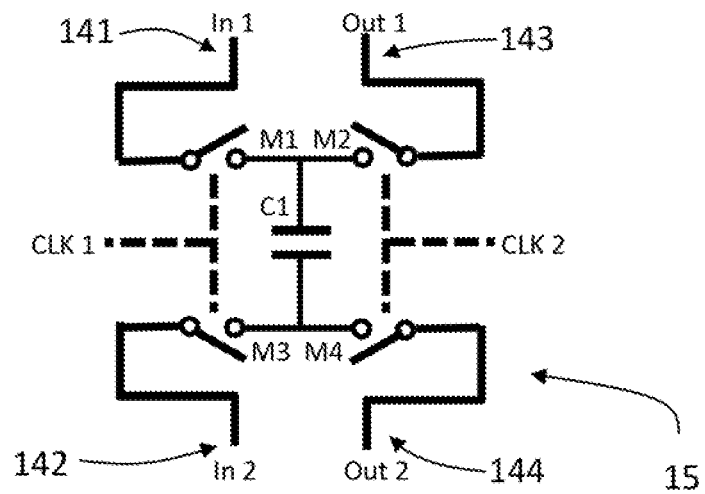
FIG. 7 is a simplified equivalent circuit of FIG. 6.
Figure 10:
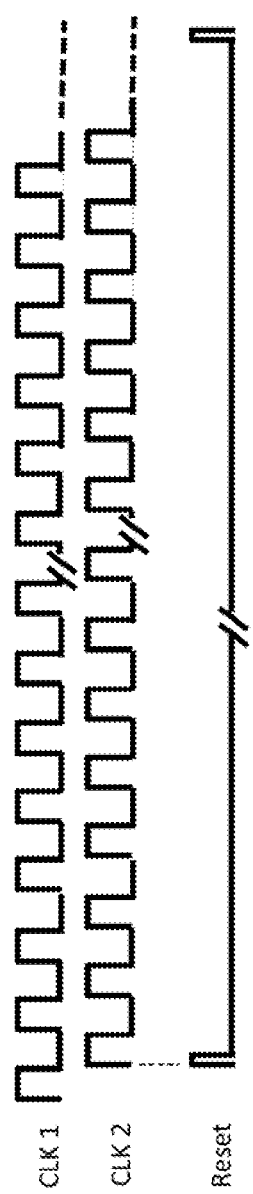
FIG. 10 is a timing diagram showing the relationship of the two non-overlapping clocks for the Switched Capacitor Circuit along with a RESET timing signal according to the preferred embodiment of the present invention.

FIG. 6 of the drawings illustrates a Switched Capacitor Circuit (SCC) 14 using four transistor switches M1, M2, M3, M4 (first through fourth transistor switch), one capacitor C1 and two non-overlapping clock CLK1, CLK2 (first non-overlapping clock and second non-overlapping clock). Each of the four transistors M1, M2, M3, M4 may have a Drain terminal, a Gate terminal, and a Source terminal. Its equivalent circuit 15 is shown in FIG. 7 of the drawings where four mechanical switches are used to represent the four transistors M1, M2, M3, M4. The timing relationship of the two non-overlapping clocking signals (CLK 1 and CLK 2) are shown in FIG. 10 of the drawings. CLK 1 and CLK 2 may control the Gate terminal of each transistor switch M1, M2, M3, M4. Note that when CLK 1 is high, CLK 2 is always low and vice versa. Both clock signals from CLK 1 and CLK 2 cannot be high at the same time, but both can be low at the same time. This non-overlapping clock relationship ensures that the SCC will have no signal leakage between its input terminal to its output terminal. When the clock signal is high, the connected transistors M1, M2, M3, M4 will be on or become conductive between the corresponding Drain and Source terminals. When the clock signal is low, the connected transistors M1, M2, M3, M4 will be off or non-conductive between the corresponding Drain and Source terminals. SCC 14 has two input terminals 141, 142 and two output terminals 143, 144, so it can process both differential and single-ended input/output signals. The clocking action of the SCC causes capacitor C1 to transfer charge from one circuit node (input) to a different circuit node (output).

Figure 8:
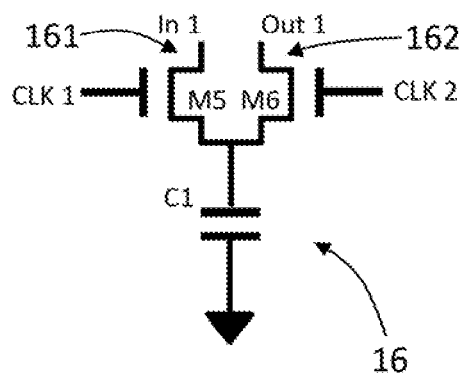
FIG. 8 is an alternative SCC circuit diagram according to the preferred embodiment of the present invention.
Figure 9:
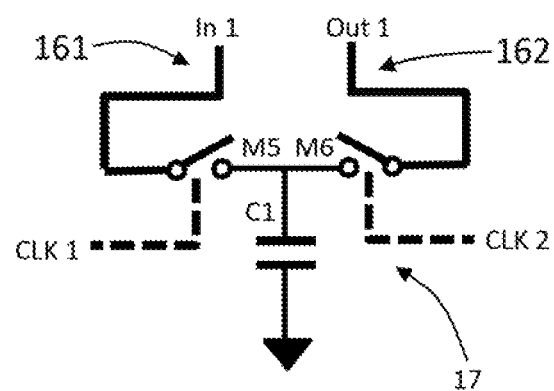
FIG. 9 is a simplified SCC equivalent circuit of FIG. 8.

In FIG. 8, SCC 16 represents an alternative circuit where the bottom plate of capacitor C1 is either connected to circuit ground or to a reference voltage. Its equivalent circuit 17 is shown in FIG. 9 of the drawings and it can only process a single-ended input and output signals. Thus, SCC 16 may have one input terminal 161 and one output terminal 162. The input terminals and the output terminals of both SCC 14 and the alternative SCC 16 are symmetrical. Therefore, the input and the output terminals of each SCC 14, 16 may be interchangeable. That is, each of the input terminals may be used as an output terminal and vice-versa, depending on layout convenience.

Circuit operation of SCC 14 of FIG. 6 will be described in detail now with the help of the equivalent circuit 15 as shown in FIG. 7 in conjunction with CLK 1 and CLK 2 of FIG. 10. When CLK 1 goes high while CLK 2 is at low, switches M1 and M3 are closed, while switches M2 and M4 are open, so the difference between the input voltage of the input terminal 141 (Vin-In 1) and the input voltage of another input terminal 142 (Vin-In 2) is being sampled by C1. When CLK 1 goes low and CLK 2 stays low, all switches (M1, M2, M3, M4) are open so C1 stores a charge corresponds to the sampled value difference between (Vin-In 1) and (Vin-In 2). The charge stored in C1 is:

$$Q = C \times V = (C1) * ((V\text{in-In}1) - (V\text{in-In}2)).$$

On the other hand, when CLK 2 goes high and CLK 1 stays low, the switches M2 and M4 are closed while M1 and M3 remain open, therefore, C1 is connected to its output nodes (the two output terminals 143, 144) and the stored charge on C1 is being made available for processing by another circuit connecting to the output terminals 143, 144 (Out 1 and Out 2). Circuit operation repeats during the next CLK 1 and CLK 2 clock interval and so on. The foregoing discussion of equivalent circuit 15 of FIG. 5 can be summarized in Table 1 below:

TABLE 1

| Step | Clock states | Switch States | Circuit Action | Note |
|---|---|---|---|---|
| 1 | CLK 1 = Hi, CLK 2 = Lo | M1, M3 = close, M2, M4 = open | C1 samples ((Vin-In 1) − (Vin-In 2)) | |
| 2 | CLK 1 = Lo, CLK 2 = Lo | M1, M2, M3, M4 = open | C1 stores Q = (C1) * ((Vin-In 1) − (Vin-In2)) | |
| 3 | CLK 1 = Lo, CLK 2 = Hi | M1, 3 = open, M2, 4 = close | C1 connects to Out 1 & Out 2; outputs Q | |
| 4 | CLK 1 = Hi, CLK 2 = Lo | M1, 3 = close, M2, 4 = open | C1 samples ((Vin-In 1) − (Vin-In 2)) | Repeat of Step 1 |
| 6 | CLK 1 = Lo, CLK 2 = Lo | M1, 2, 3, 4 = open | C1 stores Q = (C1) * ((Vin-In 1) − (Vin-In2)) | Repeat of Step 2 |
| 7 | CLK 1 = Lo, CLK 2 = Hi | M1, 3 = open, M2, 4 = close | C1 connects to Out 1 & Out 2; outputs Q | Repeat of Step 3 |

SCC 16 of FIG. 8 will be described in detail now using the equivalent SCC circuit 17 as shown in FIG. 9 in conjunction with CLK 1 and CLK 2 of FIG. 10. When CLK 1 goes high while CLK 2 is at low, switch M5 closes, while switch M6 stays open, so the input voltage of the input terminal 161 (Vin-In 1) is being sampled by C1. When CLK 1 goes low and CLK 2 stays low, both switches M5 and M6 are open so C1 stores a charge corresponds to the sampled value of Vin-In 1. The charge stored in C1 is:

$$Q = C \times V = (C1) * (V\text{in-In}1).$$

When CLK 2 goes high while CLK 1 stays low, Switch M6 closes while M5 remains open, C1 is connected to its output node (Out 1) and the stored charge is being made available for processing by another circuit connecting to the output terminal 162. Circuit operation repeats during the next CLK 1 and CLK 2 clock intervals and so on. The foregoing discussion of the equivalent SCC circuit 17 in FIG. 9 can be summarized in Table 2 below:

TABLE 2

| Step | Clock states | Switch States | Circuit Action | Note |
|---|---|---|---|---|
| 1 | CLK 1 = Hi, CLK 2 = Lo | M5 = close, M6 = open | C1 samples (Vin-In 1) | |
| 2 | CLK 1 = Lo, CLK 2 = Lo | M5 = open, M6 = open | C1 stores Q = (C1) * (Vin-In 1) | |
| 3 | CLK 1 = Lo, CLK 2 = Hi | M5 = open, M6 = close | C1 connects to Out 1 and outputs Q | |
| 4 | CLK 1 = Hi, CLK 2 = Lo | M5 = close, M6 = open | C1 samples (Vin-In 1) | Repeat of Step 1 |
| 6 | CLK 1 = Lo, CLK 2 = Lo | M5 = open, M6 = open | C1 stores Q = (C1) * (Vin-In 1) | Repeat of Step 2 |
| 7 | CLK 1 = Lo, CLK 2 = Hi | M5 = open, M6 = close | C1 connects to Out 1 and outputs Q | Repeat of Step 3 |

Figure 11:
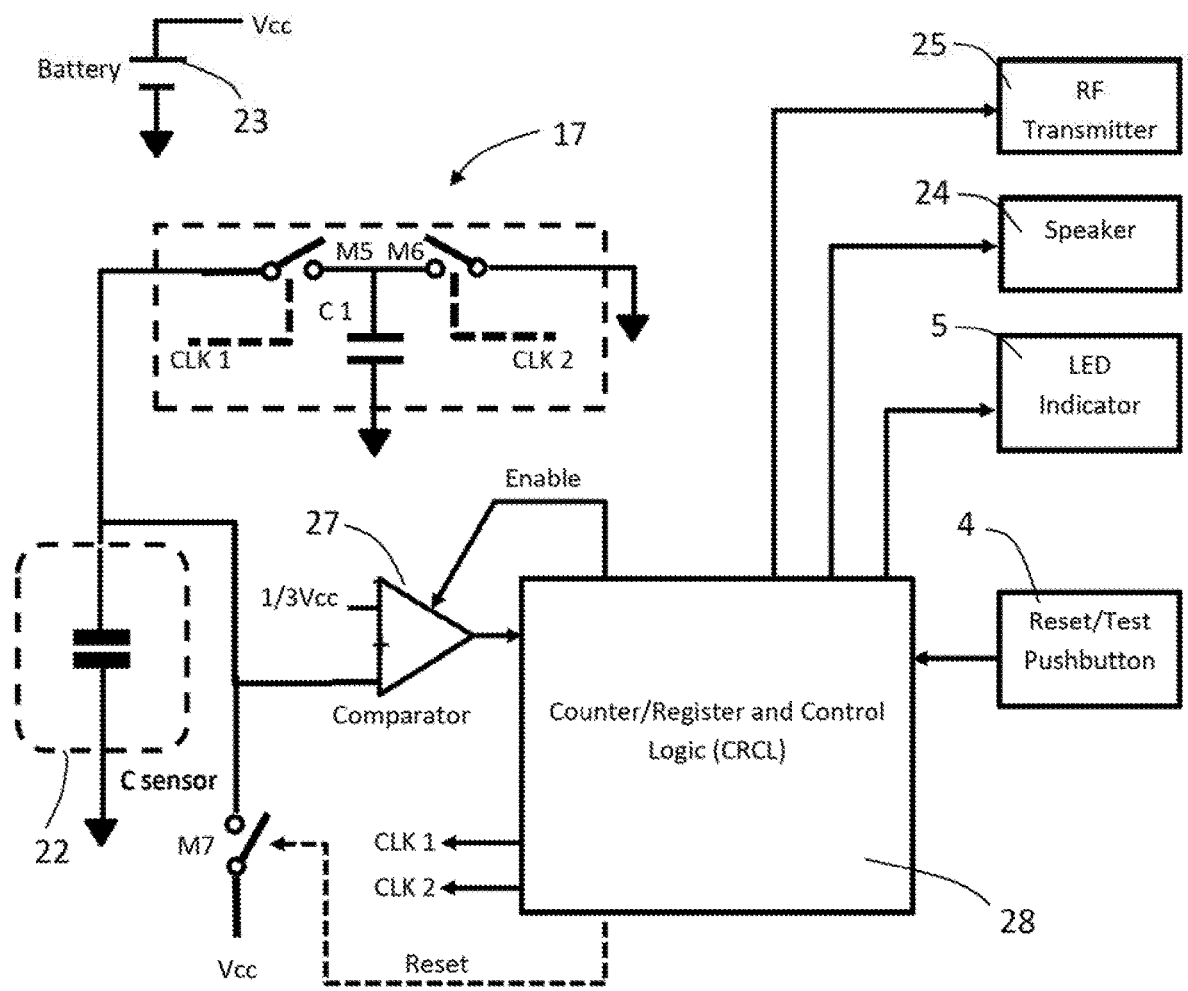
FIG. 11 is a simplified block diagram of the wet diaper monitoring device using SCC equivalent circuit according to the preferred embodiment of the present invention.

The block diagram of the preferred embodiment of the monitoring device 2 may be illustrated in FIG. 11 of the drawings. The block diagram may comprise a capacitance sensor (C sensor 22), a SCC equivalent circuit 17, a comparator 27, a Counter/Register and Control Logic (CRCL 28), a transistor reset switch (M7), a battery supply 23, the Reset/Test pushbutton 4, the LED Indicator 5, a speaker 24, and a RF Transmitter 25.

Note that the capacitor, the transistors, the digital clock circuit, the digital registers/counters, and the comparator are standard building blocks available in any MOS technology and process. The use of these standard MOS building blocks means the complete block diagram of FIG. 9, except for C sensor 22, can be integrated onto a single silicon die using standard MOS manufacturing process. Integrating a complete system or block diagram onto a single silicon die may save production cost while ensuring a more consistent product performance.

The following discussion covers in detail how a sensor capacitance (an analog value) is converted into a digital equivalent value using the arrangement shown in FIG. 11 of the drawings.

A conversion cycle to transform the sensor capacitance into a digital equivalent value requires many clock operations. A clock operation may be referred to all circuit functions or operations performed during the period consisting of a CLK 1 pulse and a CLK 2 pulse. A typical conversion may require anywhere from 50 to 500 clock operations. By design, the number of clock operations required is proportional to the capacitance ratio between C sensor 22 to C1 of the SCC 17. Circuit operation of the embodiment in FIG. 11 may be described by using the timing signals of FIG. 13 of the drawings. "Reset" signal is a periodic pulse generated by CRCL 28 to initiate conversion cycle. Its frequency is controlled by the software program. For example, the software program may initiate a new conversion every 60 seconds. This "Reset" signal indicates the beginning of a conversion cycle by initializing all internal registers and counters while charging C sensor 22 to Vcc via Switch M7. Therefore, the charge stored across C Sensor 22 at the beginning of a conversion cycle is:

$$Q0 = C\text{Sensor} * Vcc.$$

Figure 13:
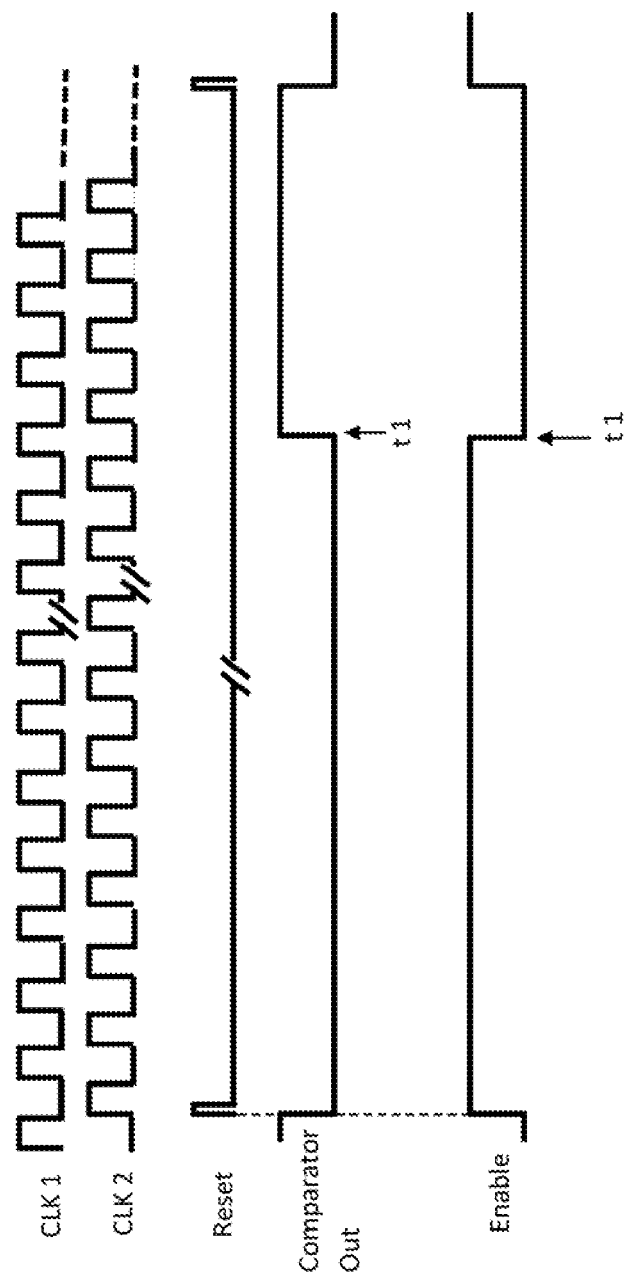
FIG. 13 is a timing diagram showing the relationship of various signals and the two non-overlapping clocks.

CRCL 28 also brings "Enable" to high, at the beginning of "Reset" signal, so Comparator 27 is enabled for voltage comparison during a conversion cycle. The timing relationship between "Reset" signal, "Enable" signal and Comparator 27 output is illustrated in FIG. 13. After "Reset" signal goes high, "CLK 2" stays high to discharge C1 to ground via Switch M6 of SCC 17. The voltage input at the "−" terminal of Comparator 27 is higher than the voltage at its "+" terminal so Comparator 27 output is low. After "CLK 2" goes low and then "CLK 1" goes high, C1 is paralleled across C Sensor 22 by Switch M5. A small portion of the charge stored on C Sensor 22 will be redistributed to C1, so $Q0 = (C\text{Sensor} \times Vcc) = (C\text{ Sensor}+C1) \times V$ C sensor, where "V C sensor" is the new voltage reading on C sensor 22 after charge redistribution with C1. Note that, by design, C1 will be hundreds of times smaller than the capacitance value of C Sensor 22. So, V C sensor is only slightly less than its previous reading but is still substantially higher than ⅓ Vcc. Therefore, Comparator 27 output is low while "Enable" is high. During this unique logic state, each positive transition of "CLK1" increments the content of a special digital counter in CRCL 28 by one-count. This special counter keeps track of the total number of "CLK 1" pulses occurred in a conversion cycle.

Figure 12:
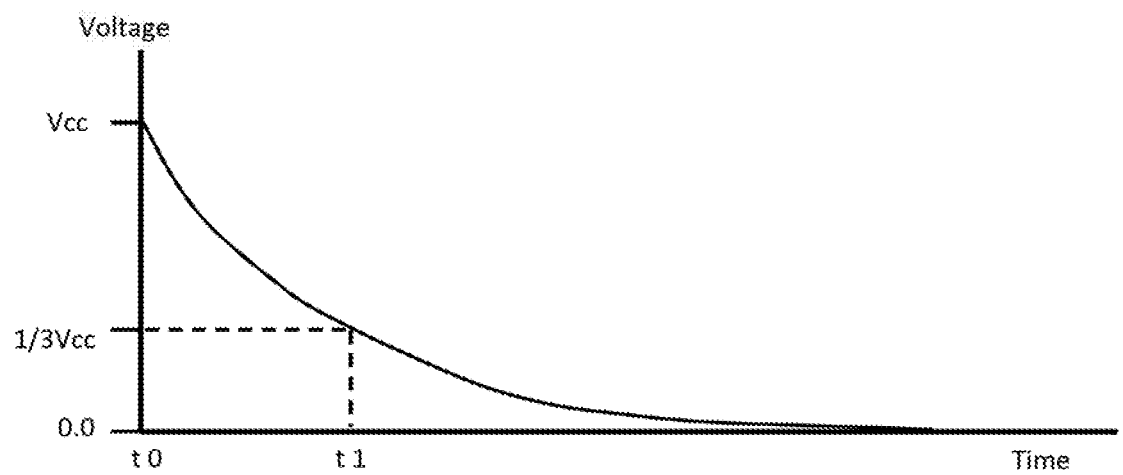
FIG. 12 is the voltage waveform of the top sensor electrode of FIG. 11.

When "CLK 1" goes low and the next "CLK 2" goes high, C1 is discharged to ground again by switch M6 while the voltage on C Sensor 22 sees no change. When "CLK 2" goes low and then "CLK 1" goes high again, C1 is paralleled across C Sensor 22 again to redistribute the remaining charge. This forces the V C sensor to go slightly lower again. The foregoing discharging and then charge redistribution process continues until V C sensor finally falls below ⅓ Vcc so the output of Comparator 27 switches from low to high. The voltage waveform across C Sensor 22 follows its classical exponential decay pattern and reaches below ⅓ Vcc at t1 as shown in FIG. 12 of the drawings. This decay time is proportional to the capacitance value of C sensor 22. The Comparator 27 output transition is captured by the logic circuit of CRCL indicating end-of-conversion. In turn, CRCL 28 would disable Comparator 27 from further operation by bringing "Enable" low. CRCL 28 also saves the content of the special digital counter that keeps track of the total number of "CLK 1" pulses. The content of this special digital counter at the end-of-conversion represents the digital equivalent value of the capacitance value of C Sensor 22.

After a diaper change and pressing of the "Reset/Test" pushbutton 4, the software program may initiate four consecutive conversion cycles to come up with four digital equivalent values, so an average digital value may be calculated. This averaged digital value is saved as a baseline reference value for comparison against new conversion results. At the end of each new conversion, the new digital equivalent value will be compared against the baseline reference value. If the new digital equivalent value exceeds the baseline reference value by a pre-determined percentage, CRCL 28 sets an internal flag signaling a soiled diaper condition is detected. Under software control, CRCL 28 can signal a LED indicator 5 and a speaker 24 for local alerting for a predetermined period or until the Reset/Test pushbutton 4 is pressed. Simultaneously, CRCL 28 may also activates RF Transmitter 25 to send out a wireless signal to notify any wireless receiver (not shown). CRCL 28 also keeps track of the elapse time when the soiled condition was first detected. If the soiled diaper is not changed within 5 minutes, CRCL 28 would send out a more urgent reminder wireless signal to alert the wireless receiver.

Software program can be implemented such that a new baseline reference value is established by calculating the running average of the latest four conversion results or readings. A new running baseline reference value obtained in this fashion can offset any slow sensor capacitance changes due to temperature effect.

Figure 15:
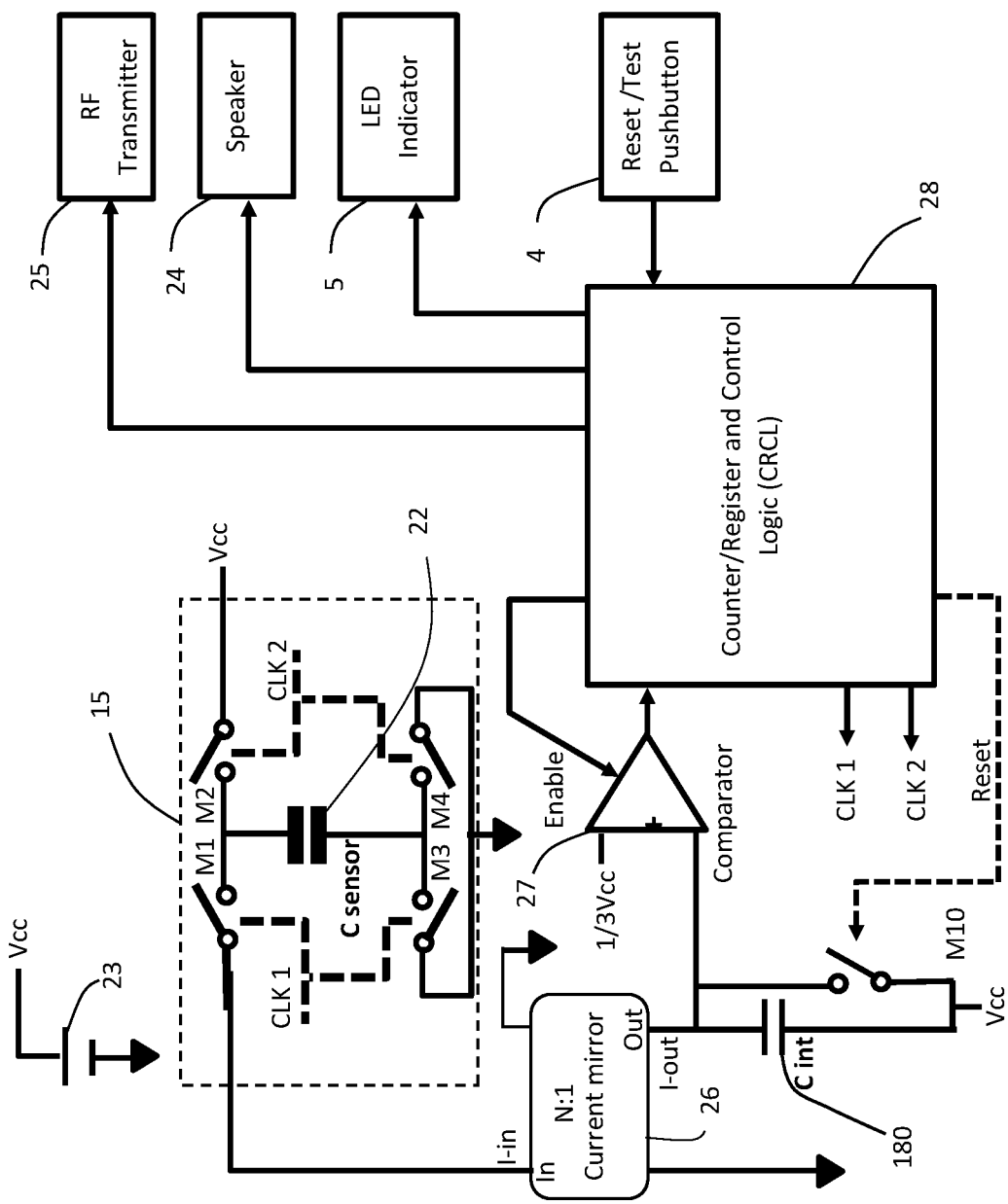
FIG. 15 is an alternative block diagram of the wet diaper monitoring device using SCC equivalent circuit and a current mirror according to the preferred embodiment of the present invention.

As shown in FIG. 15 of the drawings, an alternative circuit diagram of the monitoring device 2 is illustrated. As shown in FIG. 15, the SCC equivalent circuit 15 may comprise a C sensor 22 as the switched capacitor, a current mirror 26, an internal capacitor C int 180, a comparator 27, a Counter/Register and Control Logic (CRCL) 28, a transistor reset switch (M10), a battery supply 23, a Reset/Test Pushbutton 4, a LED Indicator 5, a speaker 24, and a RF Transmitter 25.

Switching C sensor 22 at a fixed clock rate produces an equivalent resistor according to the relationship:

$$R \text{ equivalent}=1/(C \text{ sensor}*F \text{ clk})$$

Since C sensor 22 is typically many times larger than any capacitor fabricated on a silicon chip, switching C sensor 22 at the same clock rate would produces a lower impedance across C sensor 22 than otherwise. The advantage of lower impedance means it would be less sensitive to any external noise effect or electrical interference.

Note that the internal capacitor, the transistors, the digital clock circuit, the digital registers/counters, and the comparator mentioned above may be standard MOS building blocks which may be integrated onto a single silicon die using standard MOS manufacturing process. Integrating a complete system or block diagram onto a single silicon die saves production cost while ensuring a more consistent product performance.

The following discussion covers in detail how a sensor capacitance (an analog value) is converted into a digital equivalent value using the block diagram embodiment of FIG. 15.

Figure 14:
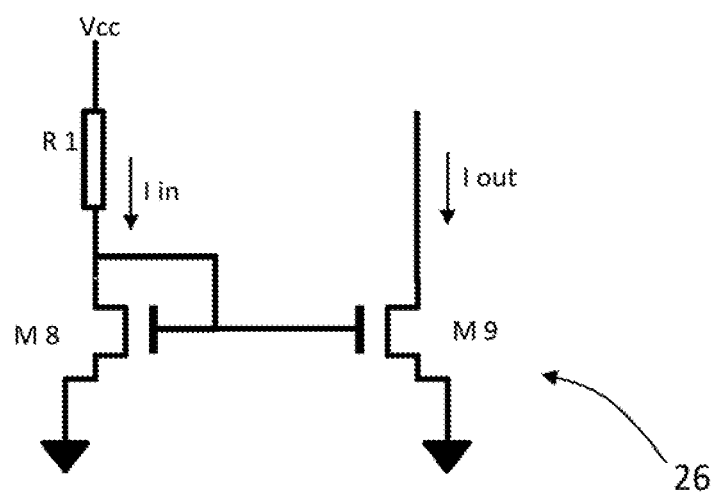
FIG. 14 is a schematic diagram of a current mirror circuit according to the preferred embodiment of the present invention.

A conversion cycle to transform the sensor capacitance into a digital equivalent value requires many clock operations. A clock operation means all circuit functions or operations performed during the period consisting of a CLK 1 pulse and a CLK 2 pulse. A typical conversion may require tens to hundreds of clock operations. For this alternative circuit diagram of FIG. 15, C sensor 22 is part of SCC 15 and is being switched by switches M1, M2, M3, and M4 under the control of CLK 1 and CLK 2. Its output is connected to the input terminal of a current mirror 26. A current mirror 26 is needed to reduce this large input current into a much smaller current, so a small internal capacitor, C int 180, can be charged or discharged in a reasonable time. The current mirror 26 may comprise two MOS transistors connected as shown in FIG. 14 where the two gates are tied to the same bias voltage. Under this condition, their drain current ratio is proportional to their respective "gate width" to "gate length" ratio or W/L ratio. By controlling this W/L ratio and by setting the input current, a controlled output current can be derived according to the following input-output relationship:

$$N=I \text{ out}/I \text{ in } =W/L \text{ output: } W/L \text{ input, where } N \text{ is set to } 0.01 \text{ in this preferred embodiment.}$$

The circuit operation of this second embodiment, FIG. 15, can best be described using the timing signals of FIG. 13. "Reset" signal is a periodic pulse generated by CRCL 28 and its frequency is controlled by the software program. This "Reset" signal indicates the beginning of a conversion cycle by initializing all internal registers and counters. CRCL 28 also brings "Enable" to high, so the comparator 27 may be enabled for voltage comparison. The timing relationship between the "Reset" signal, the "Enable" signal and the comparator 27 output is illustrated in FIG. 13 of the drawings. C int 180 is initially shorted to Vcc by switch M10.

Switching a capacitor, C sensor 22, at a fixed clock rate produces an equivalent resistor. Therefore, SCC 15 behaves as a resistor according to the following relationship:

$$R \text{ equivalence}=1/(f*C \text{ sensor}), \text{ where } f=\text{CLK1 frequency}=\text{CLK2 frequency}$$

Thus, SCC 15 may set a constant input current to current mirror 26. The output of current mirror 26 is also constant but at 100 times smaller by design. This constant output current discharges the voltage on C int 180 according to the following relationship:

$$\Delta \text{ Voltage}=(1/C\text{int})*(I\text{out}*\Delta t)$$

Figure 16:
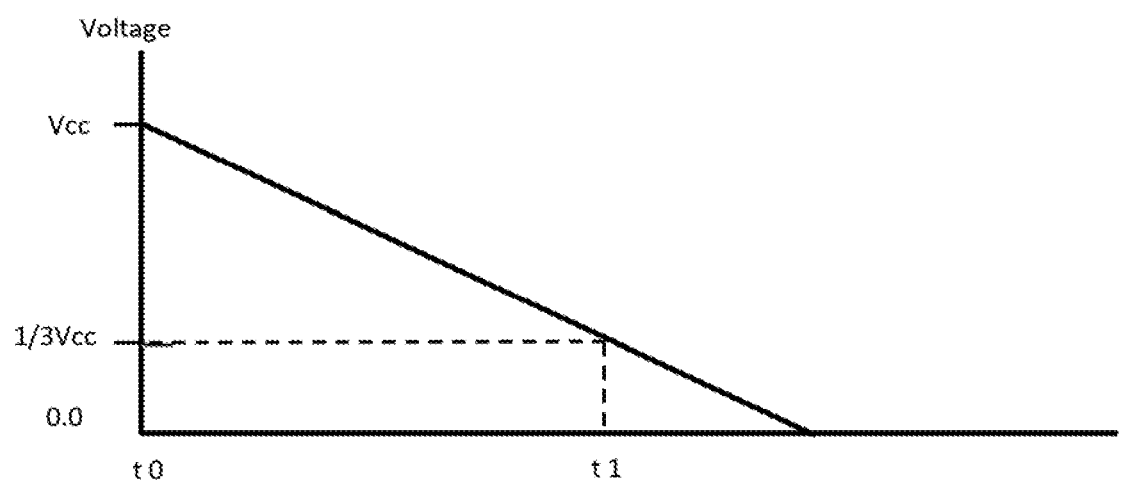
FIG. 16 is the voltage waveform on C int of FIG. 15 according to the preferred embodiment of the present invention.

Therefore, the voltage across C int 180 drops linearly from Vcc toward ground as shown in FIG. 16. The comparator 27 output stays low until the voltage on C int 180 drops just below ⅓ Vcc at t1. At that point, its output switches from low to high. This output transition informs CRCL 28 that conversion is complete. CRCL 28 immediately brings "Enable" signal low to disable Comparator 27 until the beginning of the next conversion cycle. A special digital counter inside CRCL 28 keeps track of the total number of "CLK 1" pulses occurred during a conversion while "Enable" signal is high. The content of this special digital counter at the end-of-conversion represents the digital equivalent value of the capacitance value of C Sensor 22.

Base on the nominal design value of a 5.25 pf sensor capacitance (when diaper is wet) and a clock rate of 100 Khz, a 1 pf value is needed for C int 180. It would take about 200 μsec (or 20 clock cycles) for the voltage on C int 180 to drop from 3 volt to 1 volt in FIG. 16, assume Vcc=3 volt. The calculations to derive 200 μsec are shown below:

Current mirror input current=$I$in=($V$cc−$V$threshold)/$R1$=($V$cc−1 v)/$R$ equivalence, where $V$ threshold is the current mirror input threshold voltage~1 volt for a MOS transistor, and $R$ equivalence=1/(100 Khz*5.25 pf)~2 Meg.

Therefore, Current mirror input current=$I$in=(3 v−1 v)/2 Meg=1 μA and Current mirror output current=$I$out=0.01*$I$in=0.01 μA.

→ Δ Voltage at $C$int 180=(1/$C$int)*$I$out*Δ$t$

→ Δ Voltage at $C$int 180=($V$cc−⅓$V$cc)=($I$out*Δ$t$)/$C$int 180

→ ⅔$V$cc=(0.01 ua*Δ$t$)/1 pf

→ $t$=(⅔*3.0 v*1 pf)/0.01 μA

→ Δ$t$=2*1 pf/0.01 μA

→ $t$=200 μsec

Number of clock cycle=Digital equivalent value=Δ$t$/Clock period

Digital equivalent value=200 μsec/(1/100Khz)=20 (for a wet diaper)

Similar calculations carrying out to determine the digital equivalent value for a dry diaper with a 2 pf parasitic capacitance is 52. Thus, there is a greater than 60% decrease in digital equivalent value when the diaper changes from a dry condition to a wet condition.

After a diaper change and at the press of "Reset/Test" pushbutton 4, the software program would initiate four consecutive conversion cycles to come up with four digital equivalent values, so an average digital value can be calculated. This averaged digital value is saved as a baseline reference value for comparison against new conversion results or readings.

Figure 17:
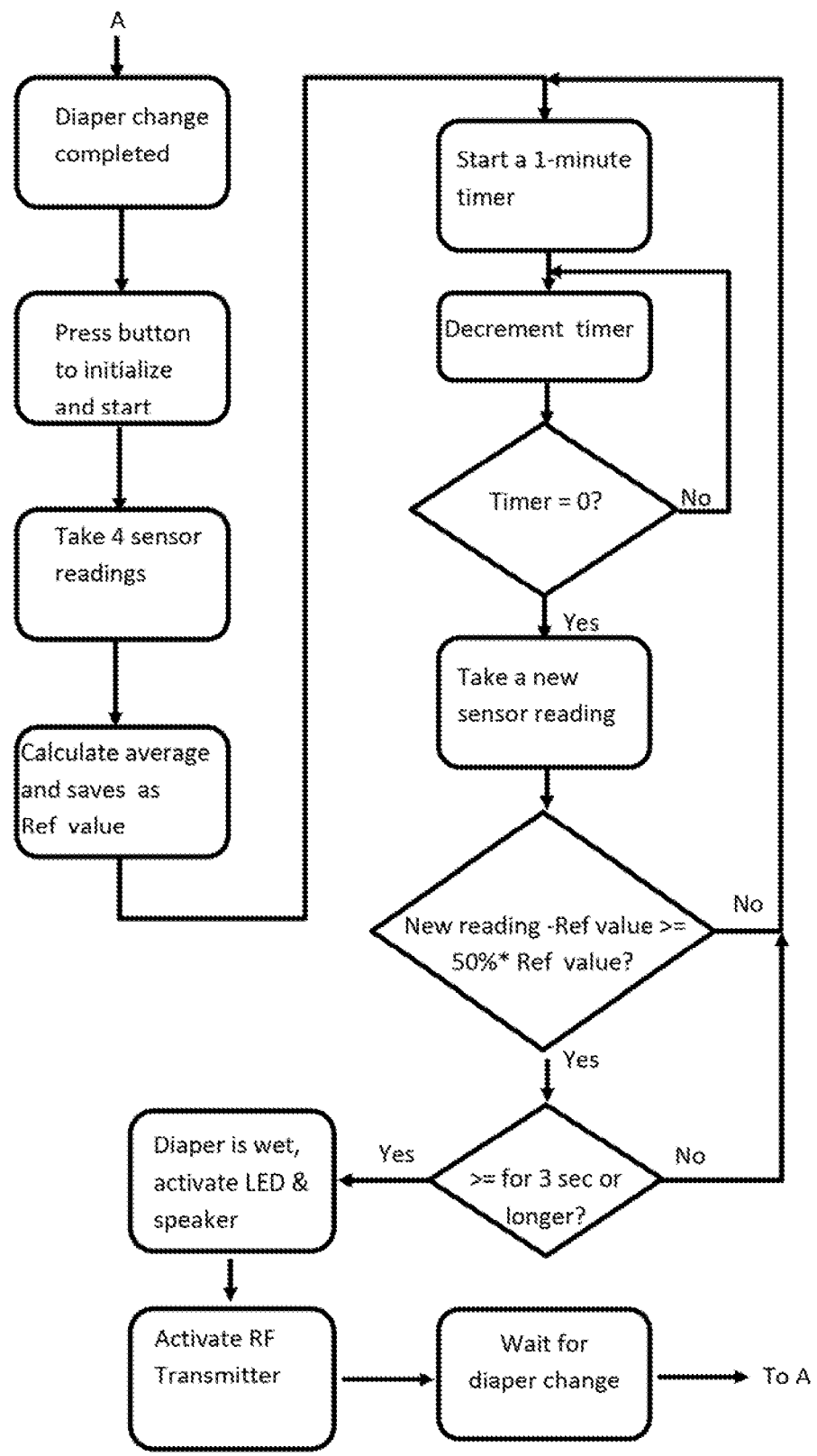
FIG. 17 illustrates a software flow chart of the wet diaper monitoring device according to the preferred embodiment of the present invention.

A wetted diaper causes C sensor 22 capacitance to increase. This would cause R equivalence to decrease. This increases the input current to the current mirror 26 and would speed up the discharging of C int 180. This shortens t1 in FIG. 16 and results in a smaller digital equivalent value accumulated in the special digital counter. A comparison of this new value against a baseline reference value is performed. If the difference exceeds a pre-determined percentage (>=30%), CRCL 28 sets an internal flag signaling a soiled diaper condition is detected. Under software control, CRCL 28 can signal the LED indicator 5 and the speaker 24 for local alerting for a predetermined period or until the Reset/Test pushbutton 4 is pressed. Simultaneously, the CRCL 28 may also activate the RF Transmitter 25 sending out a wireless signal to notify any wireless receiver (not shown). The software flow chart in FIG. 17 illustrates the approach.

As an additional feature, the CRCL 28 may also keep track of the elapse time when the soiled condition was first detected. If the soiled diaper is not changed within 5 minutes, CRCL 28 would send out a more urgent reminder wireless signal to alert the wireless receiver.

Figure 18:
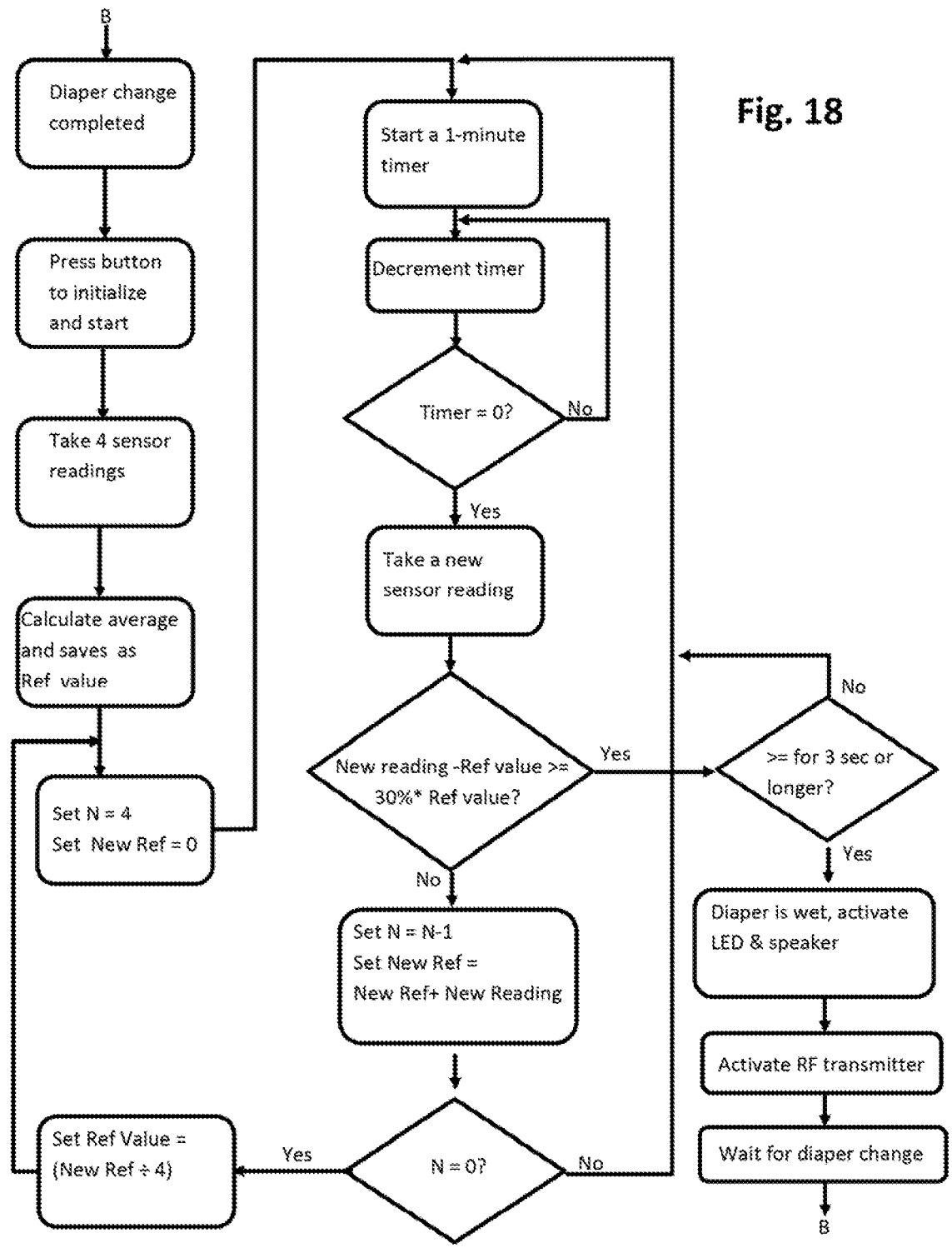
FIG. 18 illustrates a first alternative software flow chart of wet diaper monitoring device according to the preferred embodiment of the present invention.

Software program can also be implemented such that a running new baseline reference value can be established by calculating the average of the latest four conversion results or readings. A new running baseline reference value obtained in this fashion can offset slow sensor capacitance changes due to temperature effect. The software flow chart of FIG. 18 illustrates this running baseline reference value method where the average of the four latest sensor readings is calculated and set as the new baseline reference value.

Figure 19:
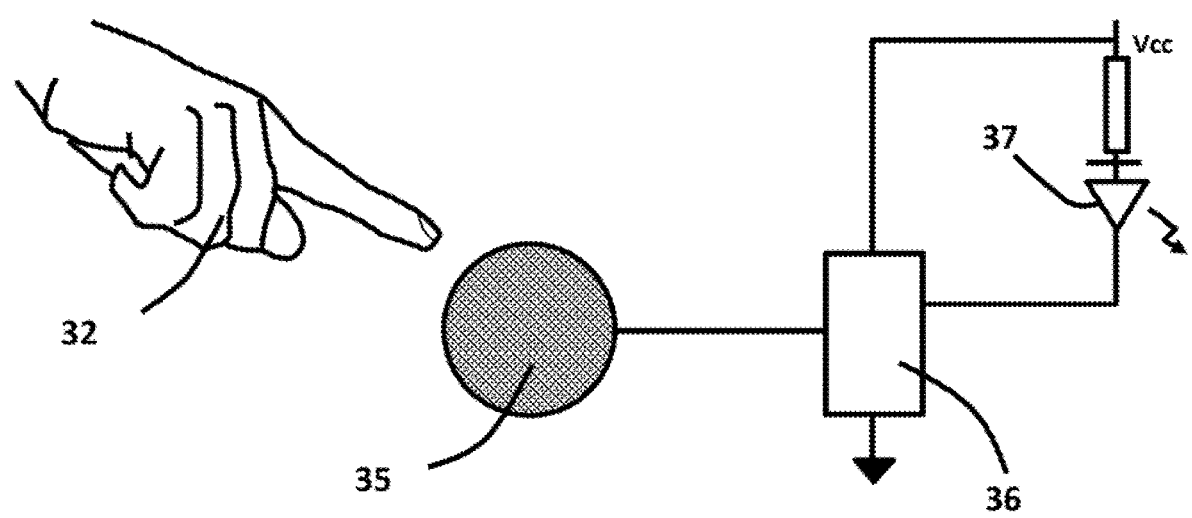
FIG. 19 illustrates a capacitance proximity/touch sensor IC detecting an approaching finger using a single electrode.
Figure 20:
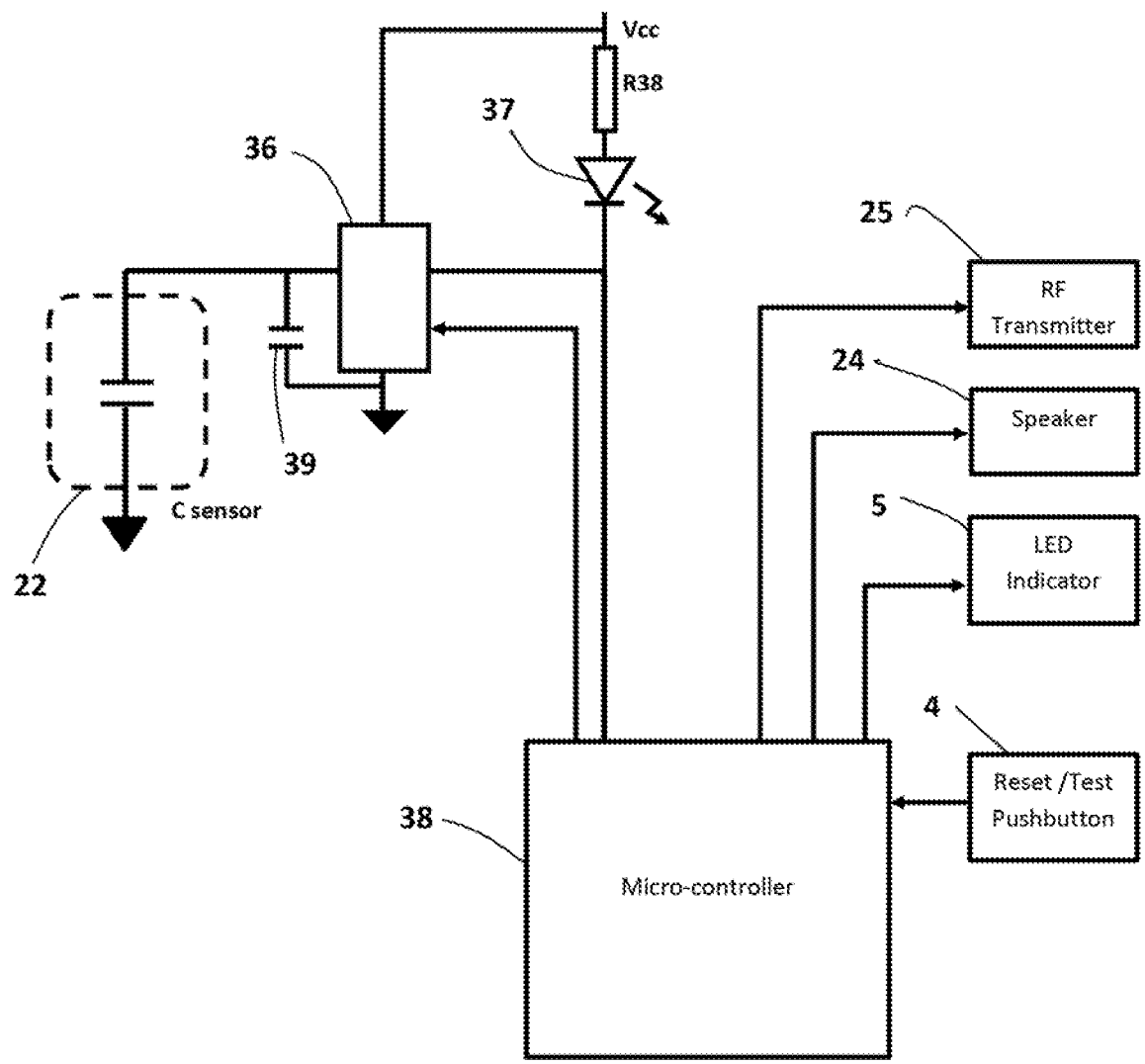
FIG. 20 illustrates a second alternative configuration of the wet diaper monitoring device according to the preferred embodiment of the present invention, illustrating that the same capacitance proximity/touch sensor IC is being modified for use as a novel electronic detector to monitor "C sensor" capacitance change by adding an input capacitor to reduce its analog input sensitivity.

As a second alternative mode of the present invention as shown in FIG. 20 of the drawings, the wet diaper monitoring device 2 may use an abundantly available low-cost capacitance proximity/touch sensor integrated circuit (IC) chip 36 as the electronic detector for the detection of the wet diaper sensor capacitance change. This represents a novel application of a capacitance proximity/touch sensor IC which is typically used for human-machine touching interface. This approach uses an off-the-shelf electronic component, which may offer significant cost advantage since no custom chip is needed. FIG. 19 shows the application of a commercially available capacitance proximity/touch sensor IC in detecting a finger touch for human-machine interface using a single sensor electrode 35. When capacitance proximity/touch sensor IC 36 detects a sudden increase in capacitance change, it momentarily activates LED 37 as a positive response indication. With the popularity of smart phone, tablet computer, ATM, and vending machine sky rocketing, many capacitance proximity/touch sensor ICs are now available for touch sensing applications. These ICs, such as a Microchip's MTCH 112, TI's FDC 1004, Standard Microsystems' STM8T141, Rohm's BU21077MUV, Azoteq IQS 118, Semtech's SX9500, Silicon Labs' CPT007B are designed to detect a very small increase in capacitance. For example, MTCH112 datasheet indicates it can detect a finger approaching from few inches away. Datasheet indicates that capacitance change less than a fraction of a pico-farad is detectable by such devices. However, if a capacitance proximity/touch sensor IC 36 is connected directly to a wet diaper monitoring device capacitance sensor, capacitance proximity/touch sensor IC 36 can be easily false triggered by the normal body movements of the diaper wearer. Therefore, its sensitivity and response time must be controlled so it is not sensitive to body movement but sensitive to a wet diaper condition. Experiment has shown that adding capacitor 39 to the input pin of capacitance proximity/touch sensor IC 36 can swamp out any stray capacitance variations caused by normal body movements of a wearer. This effectively reduces analog input sensitivity.

The response time, digital sensitivity and digital threshold of most commercially available capacitance proximity/touch sensor IC are adjustable. Experiment has shown that the combination of a slower response time, a lower digital sensitivity, and a higher digital threshold setting is essential to configuring the IC as an electronic detector of wet diaper detection.

Figure 21:
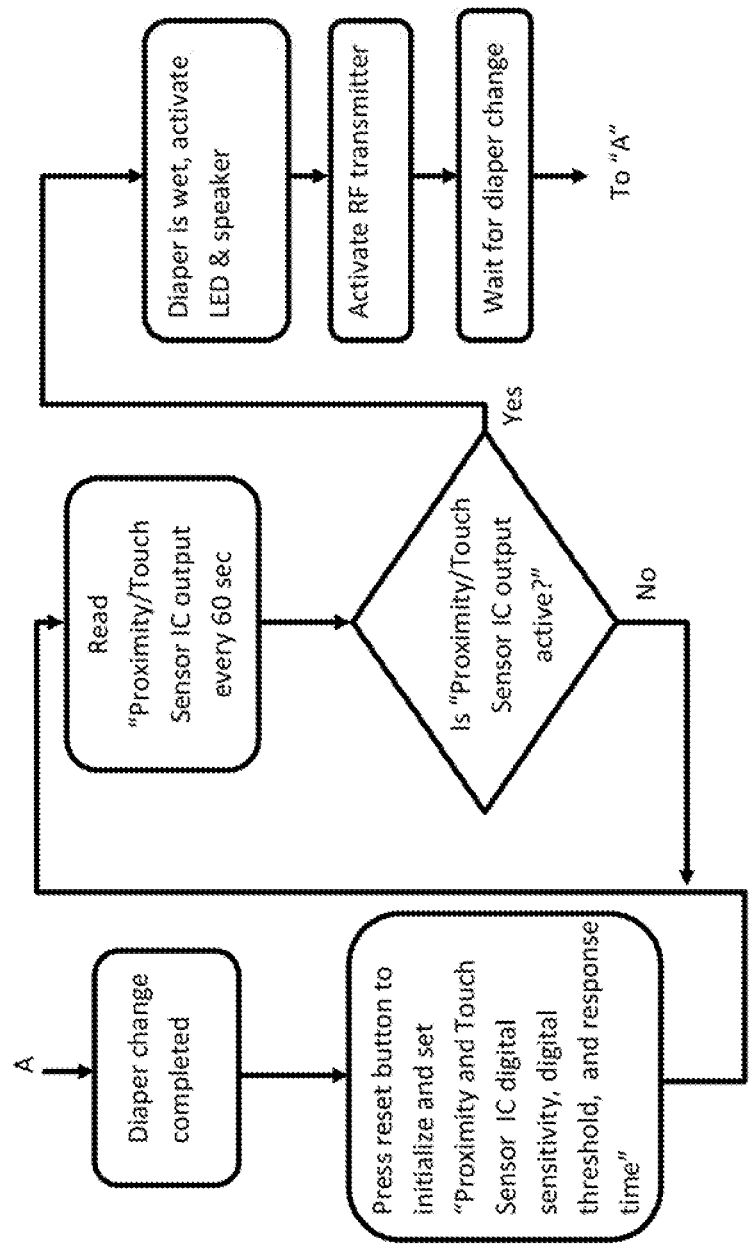
FIG. 21 illustrates a software flow chart of wet diaper monitoring device using a commercially available capacitance proximity/touch sensor IC an electronic detector for this invention.

A standard micro-controller 38 is used to interfacing with capacitance proximity/touch sensor IC 36 and other input-output controls (4, 5, 24, and 25). Micro-controller 38 interfaces with capacitance proximity/touch sensor IC 36 using standard serial bus interface. The firmware of the micro-controller programs the digital sensitivity, digital threshold and response time of capacitance proximity/touch sensor IC 36 to their proper level so any C sensor 22 capacitance change due to the physical movement of a wearer cannot cause false triggering while still sensitive in detecting a wet diaper situation. It is also possible that the commercial available capacitance proximity/touch sensor IC can be factory preprogrammed with the desired digital settings so that the micro-controller is only required to monitor its output. The combination of analog sensitivity reduction, slower response time, and lower digital sensitivity/higher digital threshold setting ensures a valid output signal only when C sensor 22 encounters a wet diaper condition. Under software control, micro-controller 38 can signal a LED indicator 5 and a speaker 24 for local alerting for a predetermined period or until the Reset/Test pushbutton 4 is pressed. Simultaneously, micro-controller 38 also activates RF Transmitter 25 sending out a wireless signal to notify any wireless receiver (not shown). The software flow chart of this third embodiment is illustrated in FIG. 21 where the digital gain and digital threshold of capacitance proximity/touch sensor IC 39 is updated when pushbutton 4 is activated after a diaper change.

As an additional feature, the micro-controller 38 also keeps track of the elapse time when the soiled condition was first detected. If the soiled diaper is not changed within 5 minutes or other preset time, micro-controller 38 would send out a more urgent reminder wireless signal for alerting.

This invention has been disclosed and described herein in terms of preferred configurations and methods. However, it will be obvious to those of skill in the art that numerous variations of the illustrated embodiments could be implemented within the scope of this invention. For example, a four-phase non-overlapping clocks may be used for SCC clocking instead of a two-phase clock, or a capacitor array may be used instead of a single capacitor SCC. Or a modified capacitance proximity/touch sensor IC with periodic calibration feature could be implemented within the scope of this invention. These and other modifications might well be made to the exemplary embodiments illustrated herein without departing from the spirit and scope of the invention.

The present invention, while illustrated and described in terms of a preferred embodiment and several alternatives, is not limited to the particular description contained in this specification. Additional alternative or equivalent components could also be used to practice the present invention.

What is claimed is:

1. A sensing circuitry for converting a capacitance value of a wet diaper capacitance sensor into a digital equivalent value, comprising:
    a switch capacitor circuit which comprises at least one capacitor, at least two transistor switches electrically connected to said capacitor, and at least two non-overlapping clocks electrically connected to said transistor switches respectively, said switch capacitor circuit having at least one input terminal electrically connected to one of said transistors, and at least one output terminal electrically connected to another of said transistor switches;

said wet diaper capacitance sensor is electrically connected to said switch capacitor circuit such that said voltage level on said wet diaper capacitance sensor is charged or discharged from a first voltage level to a second voltage level by said switch capacitor circuit;

an analog comparator having a positive input terminal, a negative input terminal, an output terminal, and an Enable terminal having an Enable signal, wherein when said Enable signal is high, said comparator is enabled for voltage comparison, wherein when said Enable signal is low, said voltage comparison is disabled;

a counter/register control logic generating said non-overlapping clocks for said switch capacitor circuit, and said Enable signal for enabling said analog comparator for operation, said switch capacitor circuit, said analog comparator, and said counter/register control logic are arranged to convert said capacitance value into said digital equivalent value for processing and decision making by said counter/register control logic, said counter/register control logic outputting a predetermined signal to drive an indicator when said digital equivalent value exceeds a predetermined value.

2. The sensing circuitry, as recited in claim 1, wherein said counter/register control logic is arranged to output a second predetermined signal to drive a speaker when said digital equivalent value exceeds a predetermined value.

3. The sensing circuitry, as recited in claim 2, wherein said counter/register control logic is arranged to output a third predetermined signal to drive a wireless transmitter when said digital equivalent value exceeds a predetermined value.

4. The sensing circuitry, as recited in claim 3, wherein said switch capacitor circuit, said analog comparator, and said counter/register control logic are integrated onto a single silicon die.

* * * * *